United States Patent [19]

Otsuka et al.

[11] Patent Number: 4,761,460

[45] Date of Patent: Aug. 2, 1988

[54] POLYMALEIMIDE COMPOUND AND COMPOSITION CONTAINING THE SAME

[75] Inventors: Masahiko Otsuka, Kurashiki; Hidekazu Ishimura, Fujinomiya, both of Japan

[73] Assignee: Asahi Kasei Kogyo Kabushiki Kaisha, Osaka, Japan

[21] Appl. No.: 21,886

[22] Filed: Mar. 4, 1987

[30] Foreign Application Priority Data

Mar. 5, 1986 [JP] Japan .................................. 61-46432

[51] Int. Cl.$^4$ ............................................. C08G 59/14
[52] U.S. Cl. .................................... 525/504; 525/530; 528/113; 528/365; 548/521
[58] Field of Search ................. 525/504, 530; 528/113, 528/365; 548/521

[56] References Cited

U.S. PATENT DOCUMENTS

| | | | |
|---|---|---|---|
| 4,288,359 | 9/1981 | Graham | 525/530 X |
| 4,296,219 | 10/1981 | Takahashi et al. | 548/521 X |
| 4,510,272 | 4/1985 | Loszewski | 525/530 X |
| 4,691,025 | 9/1987 | Domeier et al. | 548/521 |

*Primary Examiner*—Earl Nielsen

*Attorney, Agent, or Firm*—Armstrong, Nikaido, Marmelstein & Kubovcik

[57] ABSTRACT

There is provided a novel polymaleimide compound represent by the formula (a)

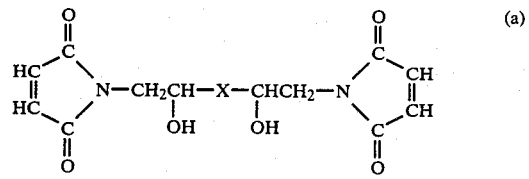

The present polymaleimide compound has a curability comparable to that of an epoxy resin. In addition, it is noted that a cured product prepared from the present polymaleimide compound is excellent in heat resistance and adhesion property and has a low linear expansion coefficient as compared with an epoxy resin. The above-mentioned excellent characteristics of the present polymaleimide compound are never observed with respect to conventional maleimide resins. There is also provided specific compositions containing the present polymaleimide compound for exerting the excellent effects of the present polymaleimide compound most effectively.

4 Claims, 1 Drawing Sheet

POLYMALEIMIDE COMPOUND AND COMPOSITION CONTAINING THE SAME

BACKGROUND OF THE INVENTION

1. Field of the Invention

The present invention relates to a polymaleimide compound and a composition containing the same which are excellent in curing characteristics, and exhibit, when cured, a high heat resistance, a low linear expansion coefficient and good adhesion characteristics, and are easily processed.

2. Background

In the fields of electric and electronic apparatus and in transportation, such as air planes and cars, as the apparatuses have become sophisticated for high performance, more compact and lighter in weight, there has been an increasing demand for a material which has a high heat resistance, is excellent in adhesion properties and has a low linear expansion coefficient.

In the fields, epoxy resins, maleimide resins, of which the typical example is N,N'-4,4'-diphenylmethane bismaleimide, polyimide resins, and the like have heretofore been used.

However, conventional polyimide resins involve a difficult problem in that they are poor in moldability due to their being insoluble in suitable solvents and infusible, although the resins are excellent in heat resistance especially in terms of glass transition point (Tg).

With respect to maleimide resins which are thermocurable, the cured resins prepared therefrom exhibit a high heat resistance and have a low linear expansion coefficient but the maleimide resins are hardly soluble in low boiling point solvents such as methyl ethyl ketone, tetrahydrofuran and the like, so that the use of special high boiling point solvents is necessary for dissolving the resins. The use of such special high boiling point solvents to form solutions of the resins therefore presents various problems For example, not only a high temperature is required for drying and removing the solvent, a small amount of which still tends to remain even after drying, but also the remaining solvent has an unfavorable influence on the properties of the cured resin products. Moreover, the adhesion properties of the cured maleimide resins are extremely poor and, therefore, the resins present difficulties in practical use.

On the other hand, epoxy resins are soluble in a low boiling point solvent and excellent in mechanical and electrical properties, and exhibits good adhesion properties as compared with maleimide resins. However, the epoxy resins have the disadvantage that they are insufficient in heat resistance and high in linear expansion coefficient as compared with maleimide resins.

Hence there has been a continuing demand for a resin which is soluble in a low boiling point solvent, and exhibits, when cured, a high heat resistance, a low linear expansion coefficient and good adhesion properties. That is, a resin which has both of merits inherent in epoxy resins and maleimide resins respectively.

To attain the required properties, there has conventionally been proposed a blended resin, e.g. a blend of an epoxy resin and a maleimide resin. The blended resin is excellent in heat resistance. However, it is poor in adhesion property as compared with epoxy resins and it exhibits only a similar solvent-solubility to those of maleimide resins, giving no solution to the above-mentioned problem. It has also been attempted to modify maleimide resins with a view to improving a solvent-solubility and adhesion properties. For example, Japanese Patent Application Laid-Open Specification No. 52-121700/1977 discloses a reaction product of an α-arylmaleimide derivative with a compound having two or more epoxy groups. From the description of the laid-open specification No. 52-121700, it is presumed that the reaction product has a structure in which the epoxy resin skeleton has its terminals to which α-arylmaleimido groups are bonded. The reaction product can be easily photopolymerized through photodimerization of the α-arylmaleimido groups. The polymerization, however, gives only a solvent-insoluble polymer, which is still poor in heat resistance. If a Michael addition reaction is tried between the reaction product and a compound having active hydrogen atoms, the reaction would not proceed smoothly due to steric hindrance of the aryl group bonded to the maleimido group, so that there could not be obtained any cross-linked product having a high heat resistance.

BRIEF SUMMARY OF THE INVENTION

With a view to providing a polymaleimide compound free from the above-mentioned drawbacks inevitably accompanying the prior art compounds, the present inventors have made extensive and intensive studies. As a result, the inventors have succeeded in obtaining a novel polymaleimide compound which is excellent in solubility in low boiling point solvents and which is capable of giving a cured product having excellent heat resistance, linear expansion coefficient, adhesion property and the like, and completed the present invention.

It is, therefore, an object of the present invention to provide a novel polymaleimide compound which is easily soluble in a low boiling point solvent and exhibits, when cured, a high heat resistance, a low linear expansion coefficient and a good adhesion property.

It is another object of the invention to provide a composition containing the novel polymaleimide compound.

The foregoing and other objects, features and advantages of the present invention will be apparent to those skilled in the art from the following detailed description and appended claims taken in connection with the accompanying drawing.

DETAILED DESCRIPTION

Figure 1:
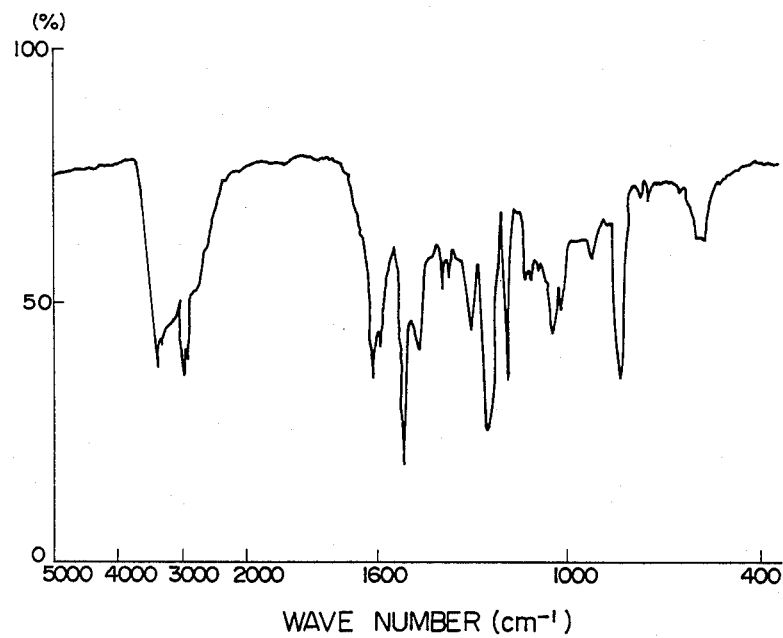
FIG. 1 is an infrared absorption spectrum of an aminoethyl hydroxyl compound (1) used as a starting material in Example 1.

In one aspect of the present invention, there is provided a polymaleimide compound having a structure represented by the formula (a):

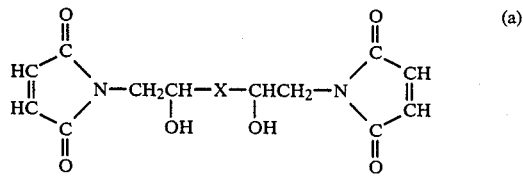

wherein X is selected from the group consisting of units represented by the formula (b) and units represented by the formula (c):

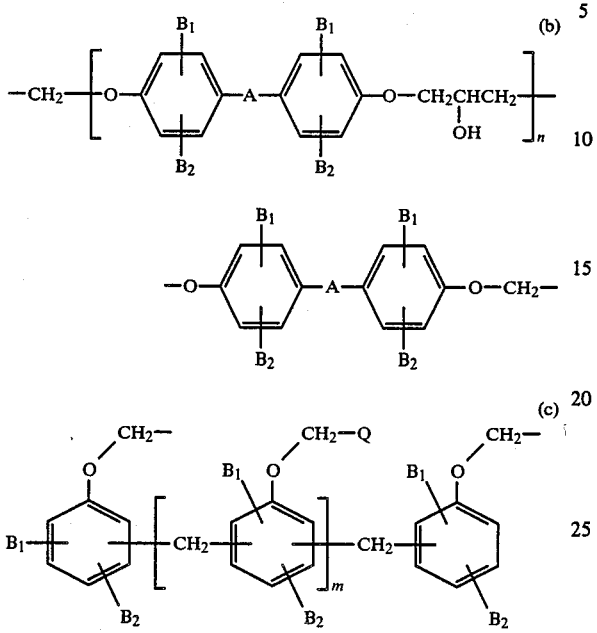

in which A is selected from the group consisting of —CH$_2$—, —C(CH$_3$)$_2$— and —SO$_2$—; B$_1$ and B$_2$ are each independently selected from the group consisting of hydrogen atom, bromine atom and methyl group; Q is a group represented by the formula

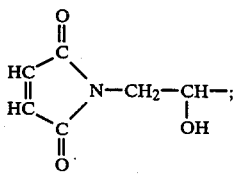

n is an integer of from 0 to 2; and m is an integer of from 1 to 10.

In another aspect of the invention, there is provided a composition comprising:

a compound (h) having at least two active hydrogen atoms on an average per molecule; and a polymaleimide compound having a structure represented by the formula (a):

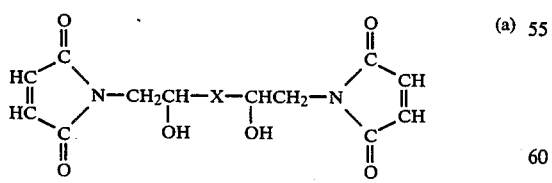

wherein X has the same meaning as defined above, and wherein the weight ratio of said compound (h) to said polymaleimide compound (a) is such that the number of the active hydrogen atoms in said compound (h) is in the range of from 0.1 to 2.0 equivalents relative to 1 equivalent of maleimido group in said polymaleimide compound (a).

In still another aspect of the invention, there is provided a composition comprising:

an epoxy compound (k) having at least two epoxy groups on an average per molecule, a compound (h) having at least two active hydrogen atoms on an average per molecule; and a polymaleimide compound represented by the formula (a):

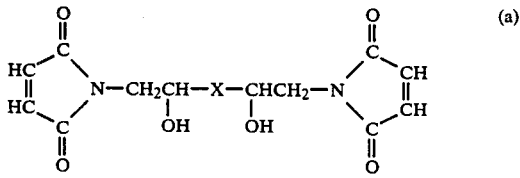

wherein X has the same meaning as defined above, and wherein the weight ratio of said epoxy compound (k) to said polymaleimide compound (a) is 5:95 to 95:5 and wherein the relationship between the maleimido groups in said polymaleimide compound (a), the epoxy groups in said epoxy compound (k) and the active hydrogen atoms in said compound (h) satisfies the equation:

$$\frac{\text{active hydrogen atoms (equivalent)}}{\text{maleimido groups (equivalent)} + \text{epoxy groups (equivalent)}} = 0.1 \text{ to } 2.0.$$

The polymaleimide compound according to the present invention is soluble in low boiling point solvents such as methyl ethyl ketone, tetrahydrofuran and the like. When the present polymaleimide compound is subjected to a Michael addition reaction with a compound having active hydrogen atoms, the reaction proceeds smoothly as opposed to the reaction using a conventional maleimide resin, exhibiting that the present polymaleimide compound has a curability as excellent as observed with an epoxy resin. In addition, it is noted that a cured product prepared from the present polymaleimide compound is excellent in heat resistance and adhesion property and has a low linear expansion coefficient as compared with an epoxy resin. The above-mentioned excellent characteristics of the present polymaleimide compound are never observed with respect to conventional maleimide resins. It is believed that the presence of hydroxyl groups and aliphatic carbon chains contributes to such excellent characteristics.

In the formula (a) of the polymaleimide compound according to the present invention, X may be a diaromatic ether residue represented by the formula (b) or a phenolic resin residue represented by the formula (c):

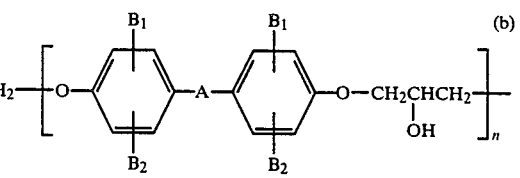

-continued

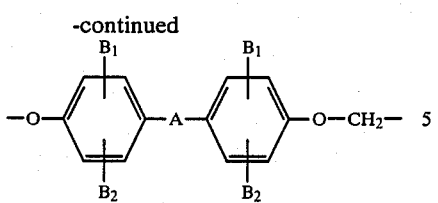

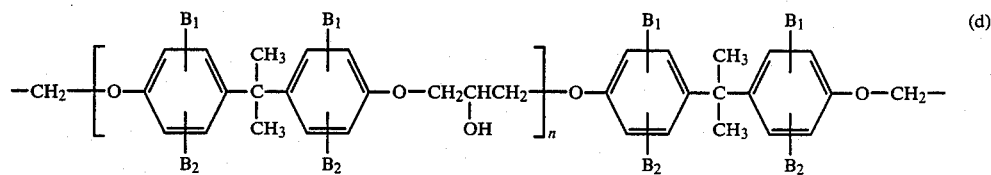

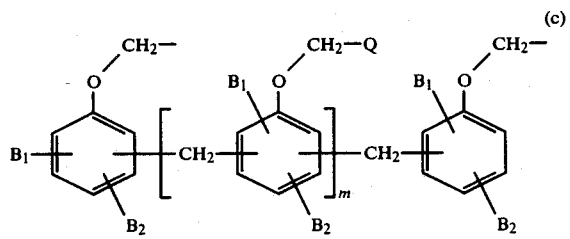

wherein A stands for a member selected from the group consisting of —CH$_2$—, —C(CH$_3$)$_2$— and —SO$_2$—; B$_1$ and B$_2$ each independently stand for a member selected from the group consisting of hydrogen atom, bromine atom and methyl group; Q is a group represented by the formula

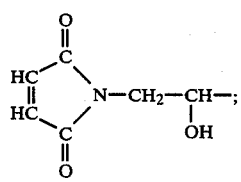

n is an integer of from 0 to 2; and m is an integer of from 1 to 10.

With respect to the polymaleimide compound having the diaromatic ether residue, it is preferred that B$_1$ and B$_2$ in the formula (b) be identical with each other from a viewpoint of desired curability, properties of the cured product and workability.

When n in the formula (b) is more than 2, the cured product is poor in heat resistance. When m is more than 10, the viscosity of the resin is increased, thereby causing a resin formulation to be difficult to handle, so that difficulties are encountered in obtaining a cured product. Therefore, m is in the range of 1 to 10, preferably in the range of 1 to 5. In this connection, it is to be noted that n and m each mean an average number of repeating units. There is no special limitation in combination of n and m.

From viewpoints of desired curability, physical properties of a cured product and workability, it is especially preferred that X in the formula (a) be a group represented by the formula (d):

which is one of the diaromatic ether residues represented by the formula (b) in which A is —C(CH$_3$)$_2$—. To attain a cured product which is more excellent in heat resistance and has still a lower linear expansion coefficient, it is more preferred that X is a group represented by the formula (e):

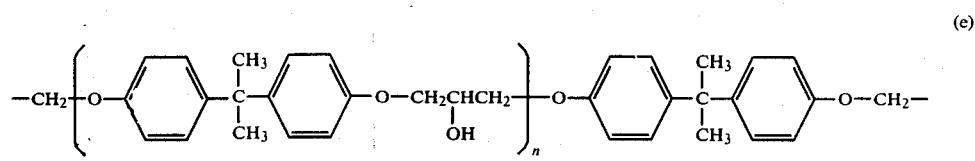

which is one of the diaromatic ether residues represented by the formula (b) in which A is —C(CH$_3$)$_2$ and both B$_1$ and B$_2$ are hydrogen atoms. For attaining much more excellent heat resistance and much lower linear expansion coefficient, it is most preferred that X in the formula (a) is a group represented by the formula (f):

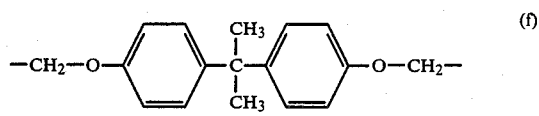

which is one of the diaromatic ether residues represented by the formula (b) in which A is —C(CH$_3$)$_2$, both B$_1$ and B$_2$ are hydrogen and n is 0.

There is no special limitation in method of preparing a polymaleimide compound according to the present invention, but from viewpoints of yield and purity of the intended compound it is preferred to employ a method in which maleic anhydride and an aminoethylhydroxy compound (g) are respectively employed as a starting material and a reactant. The aminoethylhydroxy compound (g) is represented by the following formula (g):

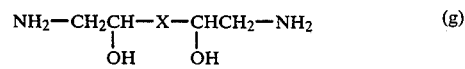

wherein X stands for a radical represented by the formula (b) or the formula (c'):

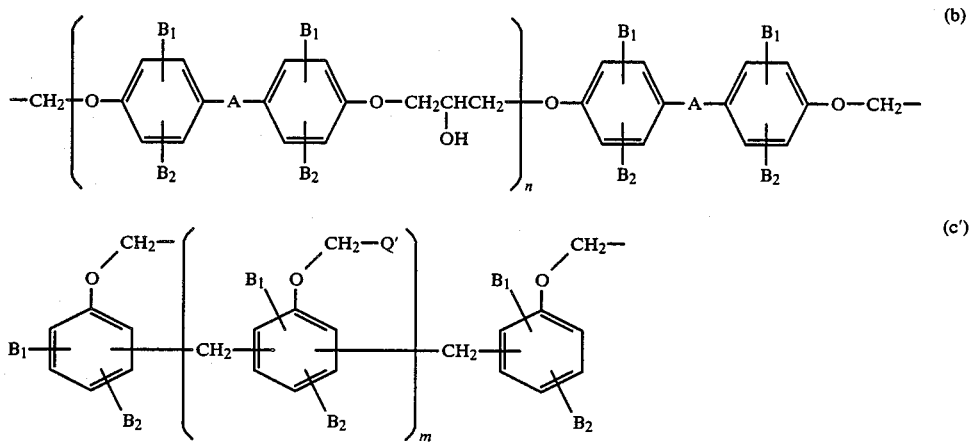

in which A stands for a member selected from the group consisting of —CH$_2$—, —C(CH$_3$)$_2$— and —SO$_2$—; B$_1$ and B$_2$ each independently stand for a member selected from the group consisting of hydrogen atom, bromine atom and methyl group; Q' is a group represented by the formula

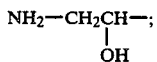

n is an integer from 0 to 2; and m is an integer from 1 to 10.

The aminoethylhydroxy compound (g) may be prepared, for instance, from an epoxy resin and aqueous ammonia as disclosed in Japanese Patent Application Publication Specification No. 49-13764/1974. The disclosed method consists in reacting an epoxy resin with aqueous ammonia at about 20° to 80° C. for 2 to 96 hours in an inert solvent. The obtained aminoethylhydroxy compound as such may be employed for a reaction with maleic anhydride without being purified. However, from viewpoints of yield and purity of the intended product it is preferred that the obtained aminoethylhydroxy compound be purified by solvent fractionation, recrystallization or the like to a purity of 70% or more and then used for a reaction with maleic anhydride.

With respect to the synthesis method involving the reaction of maleic anhydride with aminoethylhydroxy compound, the manner and reaction conditions for a known synthesis method involving the reaction of an amine with maleic anhydride may apply. That is, in the first place, an aminoethylhydroxy compound is reacted with maleic anhydride in a solvent to obtain a polyamido acid (Reaction I).

As the solvent for Reaction I, there may be employed a ketone, an alcohol, an ether, a formamide, a chlorinated hydrocarbon or an aromatic solvent. Representative examples of a ketone solvent include acetone, methyl ethyl ketone, methyl isobutyl ketone and diethyl ketone. Representative examples of an alcohol solvent include methanol, ethanol, propanol, n-butanol, isobutyl alcohol, ethylene glycol, diethylene glycol, monomethylethylene glycol, monoethylethylene glycol and monobutylethylene glycol. Representative examples of an ether type solvent include diethyl ether, di-n-propyl ether, dibutyl ether and tetrahydrofuran. Representative examples of a formamide solvent include formamide, dimethylformamide and dimethylacetoamide. Representative examples of a chlorinated hydrocarbon type solvent include dichloromethane, dichloroethane, chloroform and carbon tetrachloride. Representative examples of an aromatic type solvent include benzene, toluene, xylene and diethylbenzene. The above-mentioned solvents may be employed alone or in compatible mixture.

The reaction may be carried out at a temperature of 0° to 50° C. When the temperature is lower than 0° C., the reaction does not proceed, and when the temperature is higher than 50° C., the reaction tends to be accompanied by side reactions. A more preferred reaction temperature is 10° to 40° C. With respect to a reaction time, it may be in the range of from 0.5 to 4 hours. If the reaction is carried out for a period shorter than 0.5 hour, the reaction hardly proceeds. If the reaction is continued for a period longer than 4 hours, the reaction tends to be accompanied by side reactions. A more preferred reaction time is 1 to 3 hours. A reaction pressure is not critical, and the reaction proceeds satisfactorily at an atmospheric pressure. There is no special limitation in the manner of bringing maleic anhydride into contact with an aminoethylhydroxy compound. Maleic anhydride and an aminoethylhydroxy compound may be mixed simultaneously. Alternatively, an aminoethylhydroxy compound may be added to maleic anhydride. Preferably, the reaction is carried out while gradually adding an aminoethylhydroxy compound to maleic anhydride. The molar ratio of maleic anhydride to an aminoethylhydroxy compound may be in the range of from 1 to 2. At a molar ratio less than 1, the reaction does not sufficiently proceed, so that the terminal amino groups of the aminoethylhydroxy compound are not converted to amido acid, thus giving no intended polyamido acid derivative. At a molar ratio more than 2, it becomes difficult to purify the polyamido acid derivative produced. A more preferred molar ratio of maleic anhydride to an aminoethylhydroxy compound is in the range of 1 to 1.5.

Subsequently, the polyamido acid derivative obtained in Reaction I is subjected to dehydration-ring closure reaction (Reaction II). The reaction for dehydration-ring closure of the polyamido acid derivative may be performed using a dehydrating agent such as an acid anhydride or a carbodiimide to obtain a desired polymaleimide compound. As the dehydrating agent, it is preferred to employ an acid anhydride from viewpoints of ease of the reaction and purity of the desired polymaleimide compound. In Reaction II in which an acid anhydride is employed, a solvent need not be used, but may be used according to need. When a solvent is used, any of the above-mentioned solvents for Reaction I may be used. The solvent for Reaction I and the solvent for Reaction II may be the same or different. As the acid anhydride, there may be used an aliphatic acid anhydride or aromatic acid anhydride. As the aliphatic acid anhydride, there may be mentioned, for example, acetic anhydride, propionic anhydride and glutaric anhydride, and as the aromatic anhydride, there may be mentioned, for example, benzoic anhydride, phthalic anhydride and pyromellitic anhydride. The above-mentioned acid anhydrides may be used alone or in mixture.

Reaction II may generally be carried out at a temperature of 20° to 100° C. When the temperature is lower than 20° C., the reaction does not proceed, and when the temperature is higher than 100° C., the reaction tends to be accompanied by side reactions. A more preferred reaction temperature is 40° to 80° C. With respect to a reaction time, it may generally be in the range of from 1 to 10 hours. If the reaction time is shorter than 1 hour, no reaction proceeds, and if the reaction time is longer than 10 hours, there may occur side reactions. A more preferred reaction time is 2 to 7 hours. A reaction pressure is not critical, and usually there may be employed an atmospheric pressure. The molar ratio of acid anhydride to a polyamido acid derivative may be in the range of 1 to 10. At a molar ratio less than 1, no reaction proceeds, and at a molar ratio more than 10, it becomes difficult to purify the desired product obtained. A more preferred molar ratio is in the range of 2 to 8.

The polyamido acid derivative obtained in Reaction I may be isolated from the reaction mixture, and then, may be reacted with an acid anhydride in Reaction II. Alternatively, an acid anhydride may be directly added to the reaction mixture obtained in Reaction I containing the polyamido acid derivative, without isolation of the polyamido acid derivative. A necessary amount of an acid anhydride may be added to the polyamido acid derivative at a time or gradually.

In Reaction II, a catalyst may be used according to need. As the catalyst, a metal acetate, a tertiary amine or the like is usable. As the metal acetate, there may be mentioned, for example, sodium acetate, cobalt acetate and nickel acetate. As the tertiary amine, there may be mentioned, for example, trimethylamine, triethylamine, tripropylamine and tributylamine. They are used alone or in mixture. The catalyst may be added in an amount of 0.1 to 30% by weight based on the acid anhydride. If the catalyst is added in an amount less than 0.1% by weight, no reaction proceeds, and if the catalyst is added in an amount more than 30%, side reactions are disadvantageously liable to occur. A more preferred amount of the catalyst is in the range of from 1 to 15% by weight based on the acid anhydride.

After completion of the reaction in Reaction II, the resulting reaction mixture is washed in a large quantity of water to remove the acid components remaining unreacted. When a solvent has been used in Reaction 2, the reaction mixture may be washed in water after removal of the solvent, or may alternatively be directly washed in water without removing the solvent. The amount of water in which the reaction mixture is to be washed is not critical, and water may generally be used in an amount of 2 to 1000 times the amount of the reaction product. If the amount of water is less than twice the amount of the reaction product, it becomes difficult for the reaction product to be settled out, and if the amount of water is more than 1000 times the amount of the reaction product, difficulties are encountered in handling. A more preferred amount of water is 10 to 500 times the amount of the reaction product. This treatment of the reaction product with water may be effected at a water temperature of 0° to 80° C. If the temperature exceeds 80° C., the rate of settling-out of the reaction product is too low. A more preferred temperature of water is 10° to 60° C.

The reaction product settled out in water is filtered off, and then dried.

The thus obtained reaction product often contains other substances (impurities) than the desired polymaleimide compound. The content of the impurities in the reaction product varies depending on the reaction temperature and time, but usually may be not more than 30% by weight. The impurities can be removed by solvent fractionation, recrystallization or distillation.

The chemical structure of the polymaleimide compound according to the present invention can be identified by measuring its IR absorption spectrum and NMR. With respect to IR, an absorption peak observed near a wave number of 1700 cm$^{-1}$ and an absorption peak observed near a wave number of 690 cm$^{-1}$ are attributed to a carbonyl bond (C=O) and a carbon-carbon double bond (C=C) of a maleimido group, respectively, thereby enabling the presence of a maleimido group to be confirmed. In this connection, it is to be noted that the absorption peak observed near a wave number of 690 cm$^{-1}$ is contributed to an out-of-plane vibration of a =CH group in the cis-configuration of the present polymaleimide and is never observed in the polyamido acid derivative having a planar structure. On the other hand, by proton NMR it can be confirmed that no change has occurred in skeleton between the aminoethylhydroxy compound the resulting polymaleimide. Thus, it can be confirmed that each of the terminal groups of the aminoethylhydroxy compound is converted into a maleimido group.

The polymaleimide compound of the present invention is excellent in curability and easily soluble in a low boiling point solvent, and exhibits, when cured, a high heat resistance, a lower linear expansion coefficient and a good adhesion property. The polymaleimide compound of the present invention can be cured by heating. The polymaleimide compound as such may be heated directly, or it may be heated after it has been dissolved in a suitable solvent followed by removal of the solvent, thereby to give a cured product having excellent properties as mentioned above.

As aforementioned, in accordance with further aspects of the present invention, there are provided a composition (α) which comprises a polymaleimide compound (a) and a compound (h) having at least two active hydrogen atoms on an average per molecule and a compositon (β) which comprises a polymaleimide compound (a), a compound (h) having at least two active hydrogen atoms on an average per molecule and an epoxy compound (k) having at least two epoxy groups on an average per molecule. These compositions are provided for the purpose of exerting the excellent effects of the present polymaleimide compound (a) most effectively.

The term "compound (h) having at least two active hydrogen atoms on average per molecule" as used herein is intended to mean a compound selected from the group consisting of a non-polymeric compound having at least two active hydrogen atoms and a polymeric compound having, on average, at least two active hydrogen atoms which is capable of taking part in a Michael addition reaction with a double bond of a maleimide. Examples of the compound (h) include aliphatic amines, aromatic amines, guanidines, and phenolic resins. Representative examples of aliphatic amines include ethylenediamine, propylenediamine, butylenediamine, diethylenetriamine, triethylenetetraamine, tetraethylenepentamine, hexamethylenediamine, decamethylenediamine, dodecamethylenediamine, 2,2'-diaminopropane and 2,3'-diaminobutane. Representative examples of aromatic amines are diaminodiphenylmethane, diaminodiphenyl sulfone, m-phenylenediamine, p-phenylenediamine, triaminobenzene, o-aminobenzylamine, 2,4-diaminotoluene, triaminotoluene, benzidine, p,p'-bisaminomethylbiphenyl, p,p'-bisaminomethyldiphenylmethane, 3,3'-dichloro-4,4'-diaminodiphenylmethane and 3,3'-dimethyl-4,4'-diaminodiphenylmethane. Representative examples of guanidines are dicyandiamide, methylguanidine, ethylguanidine, butylguanidine, dimethylguanidine, trimethylguanidine, phenylguanidine, diphenylguandine and toluylguanidine. Representative examples of the phenolic resins are phenolic novolak resin and o-cresol novolak resin. They may be used alone or in mixture. From the viewpoints of the desired curing characteristics, physical properties of the cured product and workability, an aromatic amine is more preferred, and diaminodiphenylmethane, diaminodiphenyl sulfone or a mixture thereof is still more preferred. Phenolic novolak resin is also preferred from viewpoints of desired curing characteristics, physical properties of the cured product and workability.

In a composition ($\alpha$), the weight ratio of said compound (h) to said polymaleimide compound (a) may be such that the number of the active hydrogen atoms in said compound (h) is in the range of from 0.1 to 2.0 equivalents relative to 1 equivalent of maleimido group in said polymaleimide compound (a). If the above-defined number of the active hydrogen atoms is less than 0.1 equivalent or more than 2.0 equivalents, there is not obtained a cured product which is excellent in heat resistance. A more preferred number of the active hydrogen atoms is 0.5 to 1.5 equivalents. The term "equivalent" used herein means the number of maleimido groups or active hydrogen atoms.

The compound (a) is reactive with the compound (h). The reaction may proceed smoothly only by heating the composition ($\alpha$). It is preferred to effect the reaction at a temperature of 160° to 240° C. for 1 to 10 hours to obtain a cured product which is excellent in heat resistance. In this instance, there may be additionally employed polymerization of the polymaleimide compound by light or the like and/or partial polymerization of the polymaleimide compound by means of a radical polymerization initiator.

Representative examples of epoxy compound (k) having at least two epoxy groups on an average per molecule which is to be used in a composition ($\beta$) are a polyhydric phenol type glycidyl compound, a polyhydric alcohol type glycidyl compound, a carboxylic acid type glycidyl compound, an amine type glycidyl compound and a phenolic resin type glycidyl compound. Representative example of polyhydric phenol type glycidyl compound are glycidyl ethers of bisphenol A, bisphenol F, bisphenol S, catechol and resorcin. Representative examples of polyhydric alcohol type glycidyl compound are glycidyl ethers of glycerin, propylene glycol and polyethylene glycol. Representative examples of carboxylic acid type glycidyl compound are a monocarboxylic acid type glycidyl compound such as glycidyl ether esters of p-hydroxybenzoic acid and $\beta$-hydroxynaphthoic acid, and a dicarboxylic acid type glycidyl compound such as glycidyl esters of phthalic acid, terephthalic acid and dimer acid. Representative examples of amine type glycidyl compound are glycidyl amines of 4,4'-diaminodiphenylmethane, xylylenediamine and m-aminophenol. Representative examples of phenolic resin type glycidyl compound are glycidyl ethers of phenolic novolak resin and cresol novolak resin. They may be used alone or in mixture. From viewpoints of desired curing characteristics, physical properties of the cured product and workability, a polyhydric phenol type glycidyl compound is more preferred, and glycidyl ether of bisphenol A is still more preferred.

In the composition ($\beta$), it is preferred that the weight ratio of said epoxy compound (k) to said polymaleimide compound (a) be 5:95 to 95:5 and the relationship between the maleimido groups in said polymaleimide compound (a), the epoxy groups in said epoxy compound (k) and the active hydrogen atoms in said compound (h) satisfies the equation:

$$\frac{\text{active hydrogen atoms (equivalent)}}{\text{maleimido groups (equivalent)} + \text{epoxy groups (equivalent)}} = 0.1 \text{ to } 2.0.$$

If the ratio of the above-mentioned equation is less than 0.1 or more than 2.0, there is not obtained a cured product which is excellent in heat resistance. A more preferred ratio is 0.5 to 1.5.

The compound (a) is reactive with the compounds (h) and (k). The reaction may proceed smoothly only by heating the composition ($\beta$). It is preferred to effect the reaction at a temperature of 180° to 240° C. for 1 to 10 hours to obtain a cured product which is excellent in heat resistance. In this instance, there may be additionally employed polymerization of the polymaleimide compound by light or the like and/or partial polymerization of the polymaleimide compound by means of a radical polymerization initiator.

When a blend of the polymaleimide compound and the epoxy resin is subjected to heat treatment, there may often be obtained a cured product which is heterogeneous in structure due to a difference in reactivity between the polymaleimide compound and the epoxy resin. However, in the present invention, whether the cured product is homogeneous or heterogenous has no serious effects on the physical properties thereof, thereby causing no troubles in practice. In case the ratio represented by the above-mentioned equation is more than 1, the cured product is caused to contain active hydrogen atoms remaining unreacted. In the present invention, however, the remaining hydrogen atoms have no serious effects on the physical properties thereof, thereby causing no troubles in practice.

The compositions ($\alpha$) and ($\beta$) of the present invention may be prepared as follows. The components (a) and (h) for the composition ($\alpha$) or the components (a), (h) and (k) for the composition ($\beta$) are separately melted by heating and then mixed together uniformly or may be first dissolved separately in a suitable solvent and the resulting solutions are then mixed together uniformly, followed by removal of the solvent. The compositions thus obtained can be cured by heating to give cured products having excellent properties as mentioned above.

The polymaleimide compositions according to the present invention may further contain an organic solvent, a reactive diluent or a nonreactive diluent, if desired. As the organic solvent, there may be used solvents of the kind as described with respect to Reaction I. Representative examples of a reactive diluent are butyl glycidyl ether, N,N'-diglycidyl-o-toluidine, phenyl glycidyl ether, styrene oxide and ethylene glycol diglycidyl ether. Representative examples of nonreactive diluents, are dioctyl phthalate, dibutyl phthalate, dioctyl adipate and a petroleum solvent. The above-mentioned solvents and diluents may be appropriately chosen depending on the use of the composition. They may be used in an amount of about 5% by weight or more based on the composition.

The polymaleimide compositions according to the present invention may still further contain a radical initiator, a photosensitizer, a curing accelerator or a compound having a conjugated double bond, according to need. Representative examples of these classes of components are azobisisobutyronitrile and benzoyl peroxide as the radical initiator; benzophenone, benzophenone ether and Michler's ketone as the photosensitizer; a tertiary amine such as benzyldimethylamine, triethylamine and tris(dimethylaminomethyl)phenol, an imidazole such as 2-methylimidazole, 2-ethyl-4-methylimidazole and 2-phenylimidazole, and a boron trifluoride complex such as boron trifluoridemonoethylamine as the curing accelerator; and butadiene, cyclopentadiene and isoprene as the compound having a conjugated double bond. They may be appropriately chosen depending on the use of the composition. They may be used in an amount of about 0.01% by weight or more based on the composition.

The polymaleimide compositions according to the present invention may still further contain an extender, a reinforcing agent, a filler and a pigment according to need. As examples of them, there may be mentioned coal tar, glass fiber, glass cloth, asbestos fiber, boron fiber, carbon fiber, cellulose, polyethylene powder, polypropylene powder, quartz powder, mineral silicate salt, mica, asbestos powder, slate powder, kaolin, aluminum oxide trihydrate, aluminum hydroxide, chalk powder, gypsum, calcium carbonate, antimony trioxide, Pento ® (chlorinated polyether resin), silica, aerosol, lithopone, baryte, titanium dioxide, carbon black, graphite, iron oxide, gold, aluminum powder and iron powder. They may be appropriately chosen depending on the use of the composition. They may be used in an amount of about 5% by weight or more based on the composition.

The polymaleimide compound of the present invention is soluble in a low boiling point solvent, and the cured product prepared therefrom exhibits a high heat resistance, excellent adhesion property and low linear expansion coefficient. Such excellent properties have never been attained by any of the conventional materials of the similar type.

The polymaleimide compound according to the present invention has a wide variety of uses due to excellent properties of the cured products obtained therefrom. For example, the present polymaleimide compound can advantageously be used as a resin for a high density printing multilaminated substrate, as a resin for a composite carbon fiber material, and as an electric insulating material such as coil insulating material and commutator insulating material. The use of the present polymaleimide compound also includes electric materials, such as voice coil bobbin of a speaker, lamp cover of a slide projector, IC test connector and heater substrate, and electronic materials, such as die-bonding adhesive, chip-mounting material, chip-coating material and IC chip sealant. In the field of coating materials, the present polymaleimide compound can advantageously be used as a powdery coating material, electric insulating coating material and the like.

Further, as mentioned before, the present polymaleimide compound may advantageously be used in the form of a composition ($\alpha$) which comprises a polymaleimide compound (a) and a compound (h) having two or more active hydrogen atoms on an average per molecule, and a composition ($\beta$) which comprises a polymaleimide compound (a), a compound (h) having two or more active hydrogen atoms on an average per molecule and an epoxy compound (k) having two or more epoxy groups per molecule. These compositions are useful because they are capable of extremely exerting the excellent effects of the present polymaleimide compound (a) most effectively.

The present invention will be illustrated in more detail with reference to the following Examples, which should not be construed to be limiting the scope of the present invention. In the Examples, all "parts" are given by weight.

EXAMPLE 1

187 parts of an aminoethylhydroxy compound represented by the formula (1)

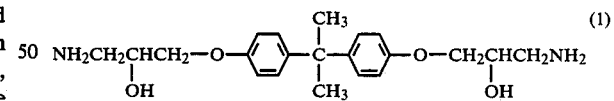

98 parts of maleic anhydride and 300 parts of tetrahydrofuran were charged in a separable flask and allowed to react at 25° C. while stirring. Two hours later the tetrahydrofuran was removed at reduced pressure. Thereafter, 32 parts of sodium acetate and 320 parts of acetic anhydride were charged in the flask and allowed to react at 60° C. for 3 hours.

After completion of the reaction, a large quantity of water is added to the reaction mixture to deposit crystals. The crystals were filtered off and dried. Then the dried crystals were subjected to extraction with ethanol using a Soxhlet's extractor. From the ethanol extract was removed ethanol to obtain a polymaleimide compound represented by the formula (1'):

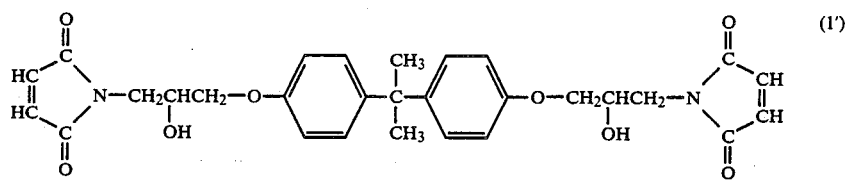 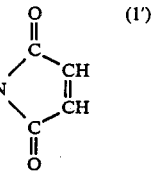

The polymaleimide compound (1') was found to have a softening point of 125° to 130° C. (measured by the method of JIS K-0064, Capillary Method). The yield of the polymaleimide compound was 85% relative to the aminoethylhydroxy compound.

Figure 2:
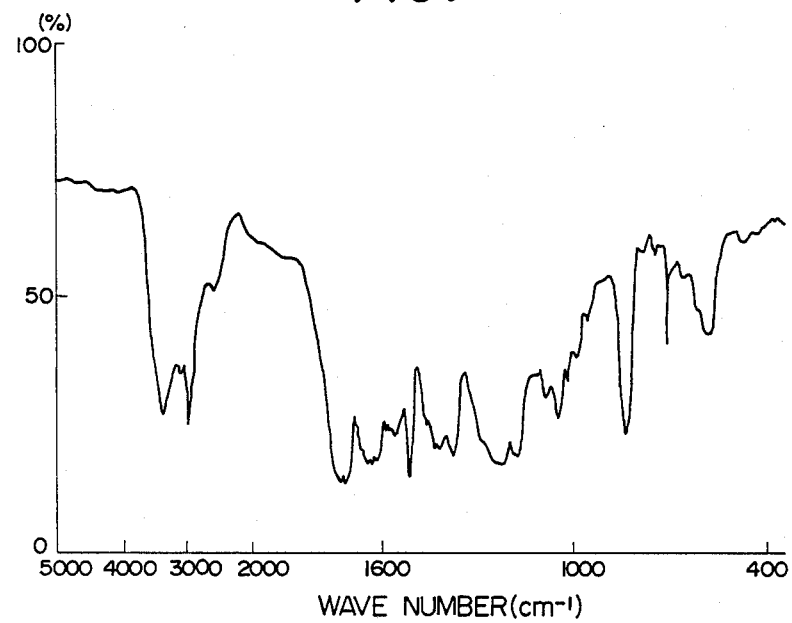
FIG. 2 is an infrared absorption spectrum of a polymaleimide compound (1') obtained in Example 1.

The obtained compound was subjected to IR analysis using an IR spectrometer (IR-430, manufactured by Shimadzu Corporation, Japan) to confirm the presence of a C=C double bond in the maleimide group near a wave number of 690 cm$^{-1}$ and a C=O carbonyl bond in the maleimide group near a wave number of 1700 cm$^{-1}$ (see FIGS. 1 and 2). The presence of groups of

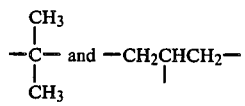

was confirmed by NMR analysis (JEOL MH100, DMSO-d$_6$) to affirm the structure of the polymaleimide compound (1').

With respect to the subsequent Examples too, the structures of the desired compounds were determined by confirming the presence of a C=C double bond and a C=O carbonyl bond which are characteristic of maleimide group by means of IR spectrometer, and confirming, by NMR, that no change in skeleton occurs between the starting compound and the desired compound except for the appearance of the carbonyl groups.

EXAMPLES 2 TO 6

Polymaleimide compounds were prepared using starting materials shown in Table 1 in substantially the same manner as in Example 1. The results are shown in Table 1. In these Examples, the amount of tetrahydrofuran employed for the preparation of a polyamido acid and amounts of acetic anhydride and sodium acetate employed for the dehydration ring closure reaction were the same as employed in Example 1. The yields of the polymaleimide compounds are indicated as percent values relative to the starting aminoethylhydroxy compounds. In each Example, structures were confirmed by IR analysis and NMR method as in Example 1.

TABLE 1
| Examples | Materials | Polymaleimide Compounds |
|---|---|---|
| Example 2 | 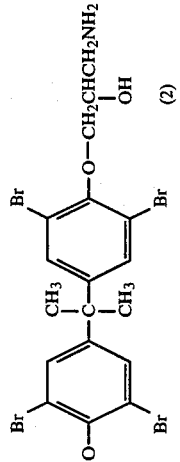 329 parts<br>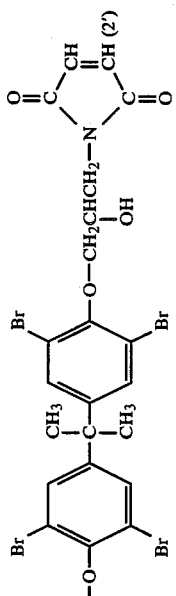 98 parts | <br>softening point: 155-165° C.<br>yield: 78% |
| Example 3 | 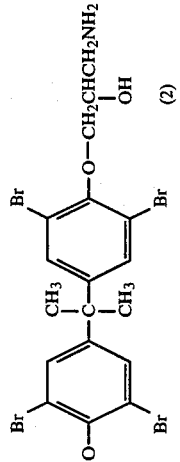 182 parts<br>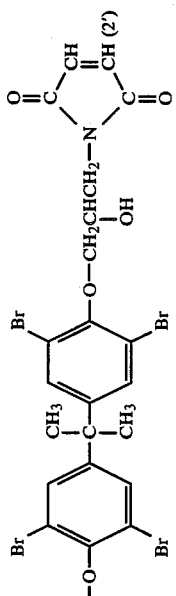 98 parts | 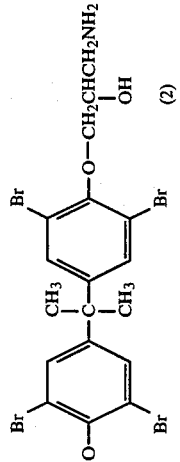<br>softening point: 165-175° C.<br>yield: 80% |

TABLE 1-continued

| Examples | Materials | Polymaleimide Compounds |
|---|---|---|
| Example 4 | (structure shown) 173 parts | (structure shown) softening point: 110–115° C. yield: 85% |
| Example 5 | (structure shown) 180 parts | (structure shown) softening point: 140–150° C. yield: 72% |

TABLE 1-continued

| Examples | Materials | Polymaleimide Compounds |
|---|---|---|
| Example 6 | ![structure with NH₂—CH₂CHCH₂(OH)—O—C₆H₄—C(CH₃)₂—C₆H₄—O—CH₂CHCH₂(OH)]ₙ linked to bisphenol-A units with O—CH₂CHCH₂(OH)—NH₂ side group (6), average of n: 2, 500 parts; and maleic anhydride (O=C—O—C=O with HC=CH), 98 parts | Polymaleimide structure (6'): [—O—C₆H₄—C(CH₃)₂—C₆H₄—O—CH₂CHCH₂(OH)—]ₙ with N-substituted maleimide side groups (N—CH₂CHCH₂(OH)—O—C₆H₄—C(CH₃)₂—C₆H₄—), average of n: 2, softening point: 90–100° C., yield: 75% |

REFERENCE EXAMPLES 1 TO 3

The solubilities of the polymaleimide compounds (1'), (3') and (5') were examined. Examination was carried out by visually observing solutions containing 50% by weight of the compounds. The evaluations were classified into three grades of solubilities, i.e., soluble, partially insoluble, and insoluble. The results are shown in Table 2.

COMPARATIVE EXAMPLE 1

N,N'-4,4'-diphenylmethane-bis-maleimide was examined with respect to solubility in substantially the same manner as in Reference Example 1. The results are shown in Table 2.

TABLE 2

| Solvent | Reference Example 1 Polymaleimide compound (1') | Reference Example 2 Polymaleimide compound (2') | Reference Example 3 Polymaleimide compound (3') | Comparative Example 1 N,N'—4,4'-diphenylmethane-bismaleimide |
|---|---|---|---|---|
| Methyl ethyl ketone | soluble | soluble | soluble | insoluble |
| Tetrahydrofuran | soluble | soluble | soluble | insoluble |
| Dimethylformamide | soluble | soluble | soluble | partially insoluble |

Test Temperature: 25° C.

EXAMPLES 7 to 10

A given amount of each of the polymaleimide compounds (1'), (2'), (3'), and (5') was melted by heating. On the other hand, a given amount of diaminodiphenylmethane as an active hydrogen compound was also melted by heating. The molten polymaleimide compound was mixed with the molten diaminodiphenylmethane. The mixture was cast in a mold and subjected to curing at 200° C. for 4 hrs. After curing, the resulting cured product was taken out of the mold to obtain a test sample. The obtained samples were subjected to determination of glass transition temperature (Tg) and linear expansion coefficient. The formulations and test results are shown in Table 3.

COMPARATIVE EXAMPLE 2

Epoxy resin AER331 (trade name of bisphenol A type epoxy resin having an epoxy equivalent of 190, manufactured by Asahi Kasei Kogyo K.K., Japan) was reacted with diaminodiphenylmethane to prepare a cured product. The prepared cured product was subjected to determination of Tg and linear expansion coefficient. The formulation and test results are shown in Table 3.

TABLE 3

| | Example 7 | Example 8 | Example 9 | Example 10 | Comparative Example |
|---|---|---|---|---|---|
| Polymaleimide compound (1'), parts | 100 | | | | |
| Polymaleimide compound (2'), parts | | 100 | | | |
| Polymaleimide compound (3'), parts | | | 100 | | |
| Polymaleimide compound (5'), parts | | | | 100 | |
| AER 331[*1], parts | | | | | 100 |
| Diaminodiphenylmethane, parts | 19 | 12 | 18 | 18 | 26 |
| Number of active hydrogen atoms/Number of maleimide group | 1/1 | 1/1 | 1/1 | 1/1 | 1/1[*2] |
| curing conditions | at 260° C. for 4 hours | | | | |
| Tg (°C.) (Vibron-[*3] measured values) | 260 | 240 | 280 | 300 | 170 |
| Linear expansion coefficient (ppm/°C.) (TMA-[*4] measured values) | 87 | 100 | 80 | 85 | 120 |

[*1] Bisphenol A type epoxy resin (epoxy equivalent: 190) manufactured by Asahi Kasei Kogyo K. K., Japan

[*2] $\dfrac{\text{Number of active hydrogen atoms}}{\text{Number of epoxy groups}}$

[*3] The glass transition point is determined by measurement of the viscoelasticity in accordance with the method described in "Kobunshi Ronbunshu" published by The Society of Polymer Science, Japan, Vol. 41 (No. 10), 605-612 (1984). A sample of cured product (5 × 1 × 50 mm) is cut out and set in VIBRON-DDV-III (apparatus produced by Toyo Baldwin K. K., Japan). Measurement of the viscoelasticity is done under such conditions that a frequency is 11 Hz, a rate of temperature elevation is 3° C./min. and a temperature range is room temperature to 300° C. The measurement gives the value of $$\text{Tan } \delta = \frac{\text{loss modulus of elasticity}}{\text{storage modulus of elasticity}}$$

The glass transition point is obtained as a value of Tan δ max.

[*4] The linear expansion coefficient is determined in accordance a method of thermomechanical analysis (TMA) described in "Kobunshi Ronbunshu" published by The Society of Polymer Science, Japan, Vol. 43 (No. 8), 529-533 (1986). A sample of cured product (5 × 5 × 10 mm) is cut out and set in a thermomechanical analyser produced by Shimadzu Corporation, Japan, and then subjected to measurement under a load of 1 g at a rate of temperature elevation of 2° C./min. The linear expansion coefficient is calculated from the gradient in the elongation.

EXAMPLES 11 AND 12

The polymaleimide compound (1') was reacted with diaminodiphenyl sulfone or a novolak type phenol resin as an active hydrogen compound to prepare cured products. The manner of preparing the cured products was substantially the same as in Example 7. The prepared cured products were subjected to determination of Tg and linear expansion coefficient. The formulations and test results are shown in Table 4.

TABLE 4

|  | Example 11 | Example 12 |
|---|---|---|
| Polymaleimide compound (1'), parts | 100 | 100 |
| Diaminodiphenyl sulfone, parts |  | 23 |
| Novolak type, phenol resin, parts | 40 |  |
| Accelerator, parts | 2-ethyl-4-methyl imidazole 0.2 | Boron trifluoride monoethylamine 0.5 |
| Number of active hydrogen/ Number of maleimide group | 1/1 | 1/1 |
| Curing conditions | at 200° C. for 6 hours | |
| Tg (°C.) | 290 | 280 |
| Linear expansion coefficient (ppm/°C.) | 80 | 75 |

TABLE 5

|  | Example 13 | Example 14 | Example 15 | Example 16 | Comparative Example 3 | Comparative Example 4 |
|---|---|---|---|---|---|---|
| Polymaleimide compound (1') parts by weight | 100 | 100 | 100 | 100 | 100 | 100 |
| Diaminodiphenylmethane parts by weight | 3.8 | 11.4 | 26.6 | 34.2 | 1.0 | 41.8 |
| Number of active hydrogen atoms/ Number of maleimide groups | 0.2/1 | 0.6/1 | 1.4/1 | 1.8/1 | 0.05/1 | 2.2/1 |
| Curing conditions |  | at 200° C. for 4 hours |  |  | at 200° C. for 4 hours |  |
| Tg (°C.) | 200 | 250 | 250 | 230 | 170 | 180 |

TABLE 6

|  | Example 17 | Example 18 | Example 19 | Comparative Example 5 |
|---|---|---|---|---|
| Polymaleimide compound (1'), parts | 100 |  |  |  |
| Polymaleimide compound (3'), parts |  | 100 |  |  |
| Polymaleimide compound (4'), parts |  |  | 100 |  |
| AER 331, parts | 100 | 100 | 100 | 100 |
| N,N'—4,4'-diphenylmethane bis-maleimide, parts |  |  |  | 100 |
| Diaminodiphenylmethane, parts | 23 | 22 | 23 |  |
| Number of active hydrogen atoms/ Number of maleimide + epoxy groups | 1/1 | 1/1 | 1/1 | 1/1 |
| Curing conditions |  | at 200° C. for 4 hours |  |  |
| Tg (°C.) | 230 | 240 | 220 | 240 |
| Shear adhesion strength Kg/cm² (JIS 6850) | 120 | 110 | 110 | 60 |

EXAMPLES 13 TO 16

In substantially the same manner as in Example 7, the polymaleimide compound (1') was reacted with diaminodiphenylmethane as an active hydrogen compound at varied ratios of number of active hydrogen atoms to number of maleimide groups to prepare cured products. The formulations and test results are shown in Table 5.

COMPARATIVE EXAMPLES 3 TO 4

Cured products were prepared in substantially the same manner as in Examples 13 to 16 except that as the ratios of number of active hydrogen atoms to number of maleimide groups, 0.05 and 2.2 were respectively employed. The formulations and test results are shown in Table 5.

EXAMPLES 17 TO 19

In substantially the same manner as in Example 7, blends of polymaleimide compounds (1'), (3') and (4') with Epoxy Resin AER 331 were cured using diaminodiphenylmethane, and the properties of the cured products were examined. The formulations and test results are shown in Table 6.

COMPARATIVE EXAMPLE 5

In substantially the same manner as in Example 7, a blend of N,N'-4,4'-diphenylmethane-bis-maleimide with Epoxy Resin AER 331 was cured using diaminodiphenylmethane, and the properties of the cured product were examined. The formulation and test results are shown in Table 6.

What is claimed is:

1. A polymaleimide compound having a structure represented by the formula (a):

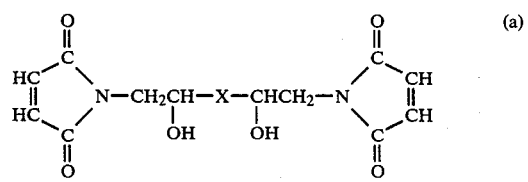

wherein X is selected from the group consisting of units represented by the formula (b) and units represented by the formula (c):

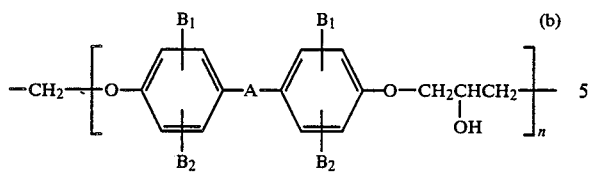
(b)

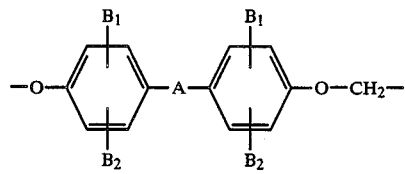
(c)

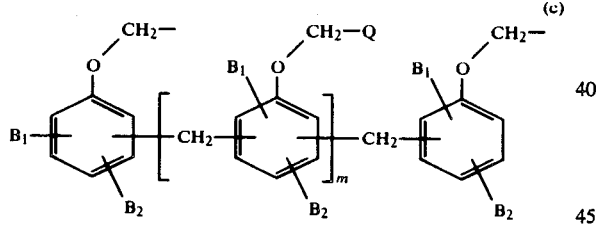
(c)

in which A is selected from the group consisting of —CH₂—, —C(CH₃)₂— and —SO₂—; B₁ and B₂ are each independently selected from the group consisting of hydrogen atom, bromine atom and methyl group; Q is a group represented by the formula

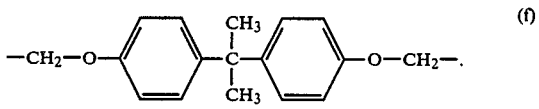

n is an integer of from 0 to 2; and m is an integer of from 1 to 10.

2. A polymaleimide compound according to claim 1, wherein X in the formula (a) is a group represented by the formula (d):

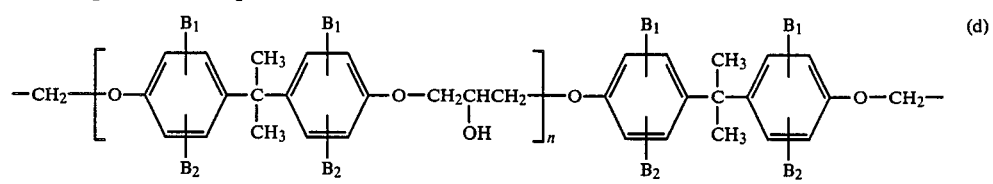
(d)

wherein B₁ and B₂ are each independently selected from the group consisting of hydrogen atom, bromine atom and methyl group, and n is an integer of from 0 to 2.

3. A polymaleimide compound according to claim 1, wherein X in the formula (a) is a group represented by the formula (e):

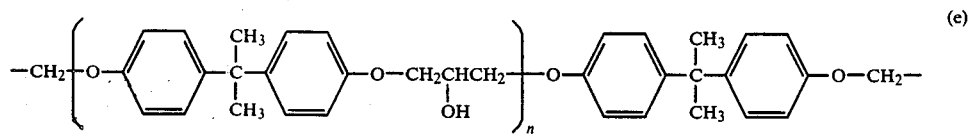
(e)

wherein n is an integer of from 0 to 2.

4. A polymaleimide compound according to claim 1, wherein X in the formula (a) is a group represented by the formula (f):

$$-CH_2-O-\underset{CH_3}{\overset{CH_3}{C}}-O-CH_2-.$$  (f)

* * * * *